US006873067B2

(12) United States Patent
Ichii et al.

(10) Patent No.: US 6,873,067 B2
(45) Date of Patent: Mar. 29, 2005

(54) LINEAR OSCILLATOR

(75) Inventors: Yoshitaka Ichii, Kadoma (JP); Katsuhiro Hirata, Kadoma (JP); Yasushi Arikawa, Kadoma (JP); Tomio Yamada, Kadoma (JP); Hidekazu Yabuuchi, Kadoma (JP); Hiroki Inoue, Kadoma (JP)

(73) Assignee: Matsushita Electric Works, Ltd., Kadoma (JP)

(*) Notice: Subject to any disclaimer, the term of this patent is extended or adjusted under 35 U.S.C. 154(b) by 522 days.

(21) Appl. No.: 09/881,693

(22) Filed: Jun. 18, 2001

(65) Prior Publication Data

US 2002/0195884 A1 Dec. 26, 2002

(30) Foreign Application Priority Data

Sep. 29, 2000 (JP) .................................. 2000-300891

(51) Int. Cl.$^7$ ............................................... H02K 33/00
(52) U.S. Cl. ........................................ 310/15; 310/36
(58) Field of Search ................................ 335/262, 263, 335/223, 233, 235, 242, 267; 310/12, 15, 17, 20, 23, 180, 181

(56) References Cited

U.S. PATENT DOCUMENTS

| | | | | |
|---|---|---|---|---|
| 3,149,255 A | * | 9/1964 | Trench | 310/30 |
| 4,169,234 A | * | 9/1979 | Yonkers | 310/29 |
| 4,422,060 A | * | 12/1983 | Matsumoto et al. | 335/256 |
| 4,549,535 A | * | 10/1985 | Wing | 601/108 |
| 4,749,891 A | * | 6/1988 | Sheng | 310/15 |
| 5,038,061 A | * | 8/1991 | Olsen | 310/15 |
| 5,104,299 A | * | 4/1992 | Mizuno et al. | 417/417 |
| 5,434,549 A | * | 7/1995 | Hirabayashi et al. | 335/229 |
| 5,809,157 A | * | 9/1998 | Grumazescu | 381/412 |
| 5,921,134 A | * | 7/1999 | Shiba et al. | 74/110 |
| 6,040,752 A | * | 3/2000 | Fisher | 335/234 |
| 2002/0195884 A1 | * | 12/2002 | Ichii et al. | 310/15 |

FOREIGN PATENT DOCUMENTS

EP    1193844 A1  *  4/2002

* cited by examiner

Primary Examiner—Karl Tamai
Assistant Examiner—David W. Scheuermann
(74) Attorney, Agent, or Firm—Oblon, Spivak, McClelland, Maier & Neustadt, P.C.

(57) ABSTRACT

A linear oscillator includes a reciprocating moving part, a case to contain the moving part, and an amplitude control spindle moveably supported in the case. The moving part and the amplitude control spindle reciprocate at a frequency approximately equal to the resonance frequency of the linear oscillator.

11 Claims, 22 Drawing Sheets

(a)

(b)

(c)

LINEAR OSCILLATOR

BACKGROUND OF THE INVENTION

1. Field of the Invention

The invention relates to a linear oscillator in which a moving part thereof reciprocates.

2. Description of the Related Art

There has been employed such a linear oscillator using a motion direction converting mechanism to convert a motor revolutionary motion into a reciprocating linear motion that can be used in a driving part for use in mechanical control or of an electric razor or a power tooth brush.

In this case, however, there would rise various problems due to a mechanical loss or noise occurring at the motion direction converting mechanism and a difficulty in miniaturization.

Besides the above, there has been known such a linear oscillator that uses no motion direction converting mechanism to reciprocate the moving part to axially by use of an electromagnetic force as well as by use of a resonance frequency determined by a spring force of a spring member having the moving part as a spring oscillation system and a mass of the moving part, however this causes high vibration because of inertia force of the moving part.

SUMMARY OF THE INVENTION

In view of the above, it is an object of the invention to provide a linear oscillator that gives a low vibration and small noise and can be miniaturized.

Thus, an aspect of the invention is a linear oscillator comprising a moving part moving reciprocally, a case containing the moving part, and an amplitude control spindle supported in the case to be movable, in which the moving part and the vibration control spindle reciprocate at a resonance frequency or in its vicinity. The amplitude control spindle is thus provided to conduct control so as to absorb or increase an amplitude due to a reaction of the moving part when it is reciprocating.

An aspect of the invention is the linear oscillator comprising an electromagnetic driving part reciprocating the moving part and a spring member making up a spring oscillation system disposed at least between the case and the moving part and between the case and the amplitude control spindle, in which a resonance frequency of the spring oscillation system is equal to that of the linear oscillator and in its vicinity.

An aspect of the invention is the linear oscillator in which the moving part and the amplitude control spindle move in phases opposite to each other and reciprocate at a resonance frequency.

An aspect of the invention is the linear oscillator in which the spring member includes a first spring disposed between a fixed part including the case and the electromagnetic driving part and the moving part, a second spring disposed between the moving part and the amplitude control spindle, and a third spring disposed between the amplitude control spindle and the fixed part.

An aspect of the invention is the linear oscillator wherein the electromagnetic driving part includes a coil, to use its coil current in order to enable controlling the reciprocating motion.

An aspect of the invention is the linear oscillator in which the electromagnetic driving part includes a coil surrounding an outer periphery of the moving part, second yokes disposed at both ends of the coil, a pair of permanent magnets which are provided at an end face of each of the second yokes and also which are magnetized symmetrically with respect to the center of the coil, and first yokes provided on the sides of the permanent magnets opposite to the second yokes.

An aspect of the invention is the linear oscillator in which a shaft for taking out a motion output is connected as a connection element to the moving part or the amplitude control spindle.

An aspect of the invention is the linear oscillator in which the second spring is stronger than the first and third springs.

An aspect of the invention is the linear oscillator in which the amplitude control spindle is provided with a rocking preventing means for preventing rocking.

An aspect of the invention is the linear oscillator in which the spring member is formed of a coil spring and the mass of the amplitude control spindle and its connection element is larger than the mass of the moving part and its connection element.

An aspect of the invention is the linear oscillator in which the spring member is formed of a leaf spring and the mass of the amplitude control spindle and its connection element is smaller than the mass of the moving part and its connection element.

An aspect of the invention is the linear oscillator in which at least a portion facing the electromagnetic driving part in the case is formed of an electromagnetic substance and the thickness of the portion facing the electromagnetic driving part is 7% or larger of an outer diameter of the permanent magnet.

An aspect of the invention is the linear oscillator in which a magnetic flux increasing means is provided which increases magnetic flux running toward the moving part.

An aspect of the invention is the linear oscillator in which a first yoke has a triangular cross section which has its sloped side facing the case.

An aspect of the invention is the linear oscillator in which part or the whole of the shaft is made of a nonmagnetic substance.

An aspect of the invention is the linear oscillator in which only a portion of the moving part passing through the shaft is made of a nonmagnetic substance.

An aspect of the invention is the linear oscillator in which the yoke or the moving part is provided with an eddy current loss reducing means for reducing an eddy current loss.

An aspect of the invention is the linear oscillator in which the moving part has an amplitude-directional slit formed therein.

An aspect of the invention is the linear oscillator in which the moving part has a large diameter portion at its both ends in its reciprocating direction and a small diameter portion at its center in such a configuration that a boundary between the large diameter and small diameter portions roughly agrees with the end faces of the second yokes on the side of the coil and both end faces of the moving part in its reciprocating direction roughly agree with the end faces of the permanent magnets on the sides of the first yokes respectively.

An aspect of the invention is the linear oscillator in which a gap between the outer circumferential surface of the moving part and the inner circumferential surface of the yoke is non-uniform in an revolutionary direction.

An aspect of the invention is the linear oscillator including comprising a revolution restricting means for restricting revolution of the shaft.

An aspect of the invention is the linear oscillator in which the spring member acts as the revolution restricting means.

DETAILED DESCRIPTION OF THE PREFERRED EMBODIMENTS

Figure 1:
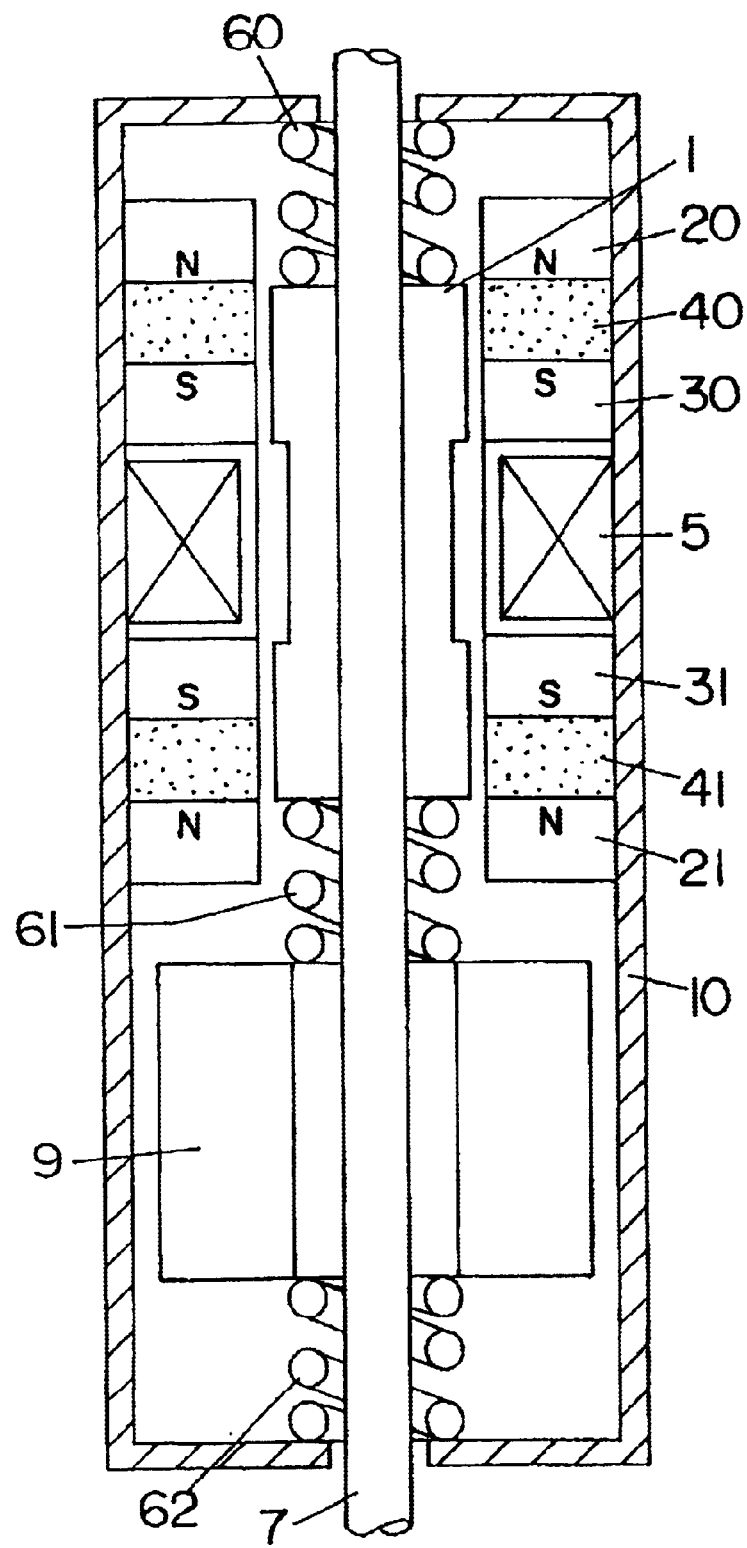
FIG. 1 is a cross-sectional view of one embodiment of the invention.

FIG. 1 shows one embodiment of the invention, in which a cylindrical plunger 1 made of a magnetic substance such as iron constituting the moving part housed in the case has a large diameter at its both ends and a small diameter at its center in such a configuration that through the plunger 1, an output-take-out shaft 7 is pierced and fixed therein as a connection element and on the periphery of the plunger 1 is provided a coil 5. At both axial ends of the above-mentioned annular coil 5 fixed on the inner surface of a shield case 10 acting as the case are provided annular permanent magnets 40 and 41 magnetized symmetrically with respect to the coil 5, so that between the magnets 40 and 41 and the coil 5 are provided annular second yokes 30 and 31, and on the sides of the magnets 40 and 41 opposite to the yokes 30 and 31 are provided annular first yokes 20 and 21 respectively. Those coil 5, permanent magnets 40 and 41, and yokes 30, 31, 20, and 21 are combined to make up an electromagnetic driving part. Between one end face of the above-mentioned plunger 7 and the shield case 10 is provided a spring 60, while between the other end face of the plunger 7 and the shield case 10 are provided a spring 61, an amplitude control spindle 9, and a spring 62 in this order. A spring member (springs 60, 61, and 62) is provided as a spring oscillation system for energizing the moving part axially, supporting the amplitude control spindle to the case to be movable. The plunger and the amplitude control spindle reciprocate at a resonance frequency of the spring oscillation system. This resonance frequency is equal (or vicinal) to that of the linear oscillator. Although the spring member (springs 60, 61, and 62) employs a coil spring easy to obtain a relatively large amplitude, any other appropriate springs may be used.

When the coil 5 has no current flowing therethrough, the plunger 1 stands still at a shown position where a magnetic force which the permanent magnets 40 and 41 have on the plunger 1 via the yokes 20, 30, 21, and 31 is balanced with a spring force of the springs 60, 61, and 62. When the coil 5 has a current flowing in one direction therethrough, the magnetic flux of either one of the two permanent magnets 40 and 41 is weakened and so the plunger moves toward the other magnet as against the force of the spring 60, and when the coil 5 has a current flowing in the opposite direction therethrough, on the other hand, the plunger 1 still moves in the opposite direction, so that by flowing an alternating current through the coil 5, the plunger 1 reciprocates axially, thus enabling controlling of the reciprocating motion by a coil current.

Figure 2:
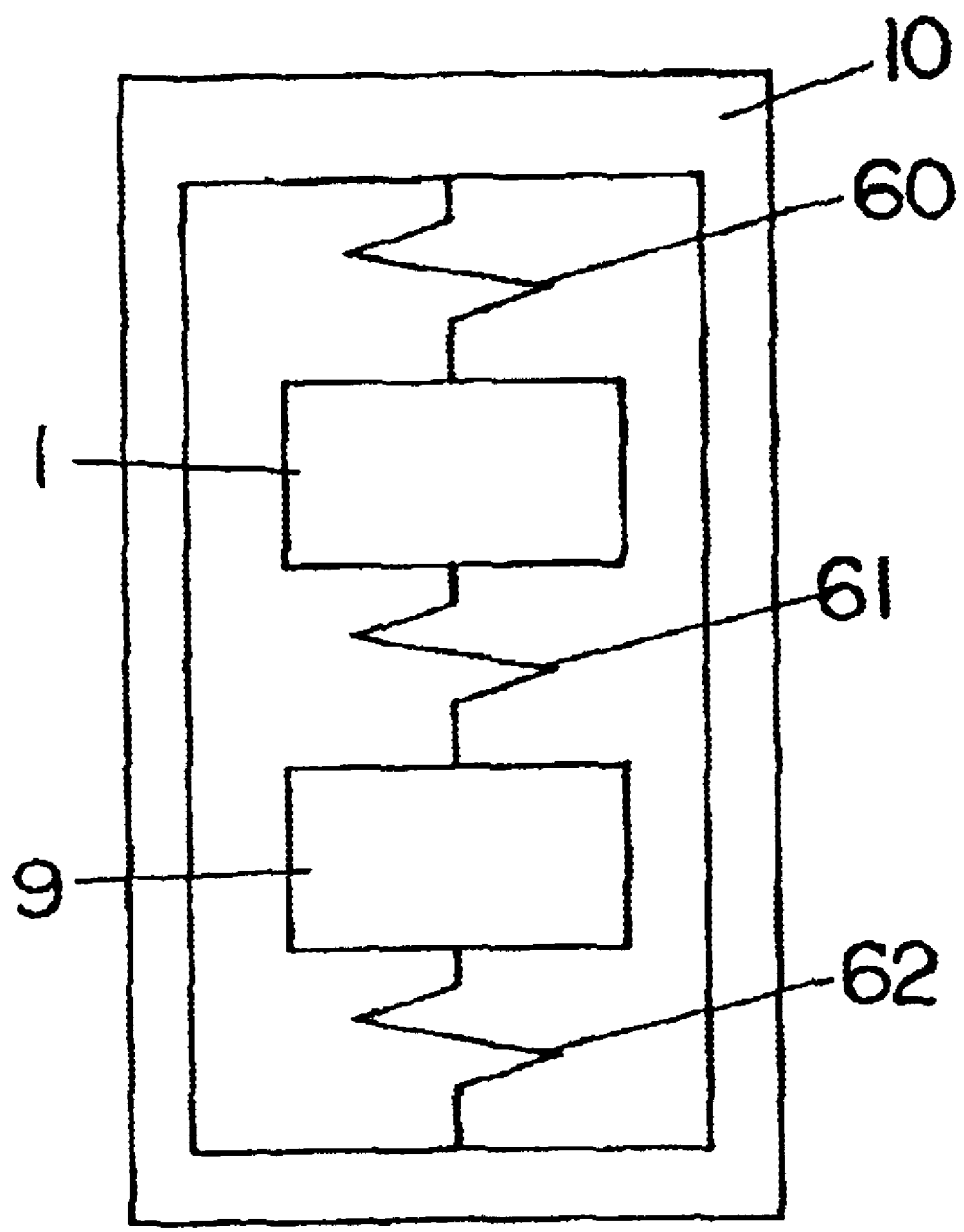
FIG. 2 shows a model of the embodiment.

If, in this case, attention is paid to the axial motion of such moving parts as the plunger 1, the shaft 7, and the amplitude control spindle 9, it is known that there are provided the above-mentioned springs 60, 61, and 62 made up of a coil spring to permit this linear oscillator to be handled as such a three-mass-point system oscillation modes as shown in FIG. 2, so that if it is assumed that the electromagnetic driving part having the coil 5 as the main body and the shield case 10 act as the fixed part and that m1 represents mass of the moving part, m2 represents mass of the vibration control spindle, m3 represents mass of the fixed part, k1 represents a spring coefficient of the spring 60, k2 represents a spring coefficient of the spring 61, k3 represents a spring coefficient of the spring 62, c1 represents an attenuation coefficient of the spring 60, c2 represents an attenuation coefficient of the spring 61, and c3 represents an attenuation coefficient of the spring 62, the motions at the time of free oscillation of those three mass points of the above-mentioned oscillation system can be determined by motion equations (1), (2), and (3) and also, if values of m1=m2, k1=k3, c1=c3, and m3 is sufficiently large as compared to m1 and m2, equations (4) and (5) can be solved by solving the above-mentioned equations, where the attenuation term is omitted in the equations (4) and (5).

$$m1\ddot{x}1 + c1(\dot{x}1 - \dot{x}3) + c2(\dot{x}1 - \dot{x}2) + k1(x1 - x3) + k2(x1 - x2) = 0 \quad (1)$$

$$m2\ddot{x}2 + c2(\dot{x}2 - \dot{x}1) + c3(\dot{x}2 - \dot{x}3) + k2(x2 - x1) + k3(x2 - x3) = 0 \quad (2)$$

$$m3\ddot{x}3 + c1(\dot{x}3 - \dot{x}1) + c3(\dot{x}3 - \dot{x}2) + k1(x3 - x1) + k3(x3 - x2) = 0 \quad (3)$$

-continued $$f1 = \frac{1}{2\pi}\sqrt{\frac{k1}{m1}} \quad (4)$$

$$f2 = \frac{1}{2\pi}\sqrt{\frac{k1+2k2}{m1}} \quad (5)$$

Frequencies f1 and f2 thus obtained as two solutions are each a resonance frequency and, therefore, in an oscillation mode of the resonance frequency f1 of the primary side (lower order side) of Equation (4) the moving part and the amplitude oscillation spindle 9 move in a same phase and in an oscillation mode of the resonance frequency f2 of the secondary side (higher order side) of Equation (5) the moving part and the amplitude control spindle 9 move in phases opposite to each other; so that when the moving part is reciprocated axially by flowing through the coil 5 a current having a frequency in the vicinity of this secondary side resonance frequency f2, the amplitude control spindle 9 moving in the opposite phase cancels inertia force of the moving part, which in turn cancels an inertia force of the amplitude control spindle 9. In this state, further, the two mass points of the moving part and the amplitude control spindle 9 would move so as to balance their respective inertia forces to thereby give a great effects of canceling the inertia forces by means of the counteraction, thus minimizing the force transmitted from these two mass points (the moving part and the amplitude control spindle 9) to the fixed part side hence the amplitude of the linear oscillator.

As may be obvious from the above equation (5), to keep the secondary side resonance frequency f2 at a constant value, it is necessary to set the spring coefficient k2 of the spring 61 at a large value and the spring coefficients k1 and k3 of the springs 60 and 62 at small values. If the spring coefficients k1 and k3 of the springs 60 and 62 respectively are thus set smaller, the amplitude control spindle 9 receives a less force from the fixed part, resulting in a larger stroke of the moving part.

Also, the mass of the amplitude control spindle 9 should preferably be larger than that of the moving part. This is because, when they move in the vicinity of the secondary side resonance frequency f2, the two mass points of the moving part and the amplitude control spindle 9 would move so as to balance their inertia forces, so that the moving part having smaller mass obtains a larger oscillation amplitude than the amplitude control spindle 9 having larger mass, thus making it possible to increase the stroke of the moving part. If they move at the lower order side resonance frequency, on the other hand, the amplitude control spindle and the moving part move in the same direction, thus making it possible to increase the amplitude of the moving part. Also, if it is possible to move them at alternating frequencies of the lower order and higher order sides, a stroke increase and an amplitude increase can be switched according to the application.

Figure 3:
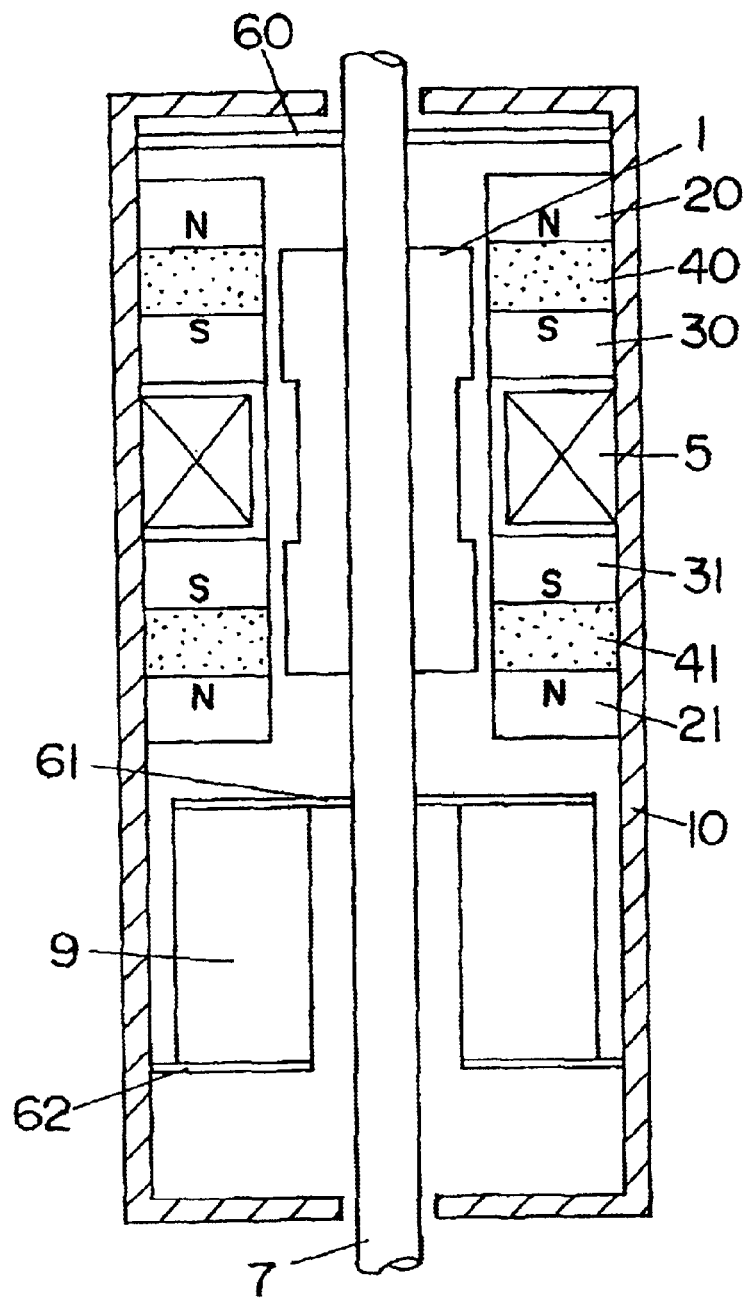
FIG. 3 is a cross-sectional view of another embodiment of the invention.

FIG. 3 shows another embodiment. In this embodiment, the springs 60, 61, and 62 are all made of a leaf spring. In this case, the mass of the amplitude control spindle 9 should preferably be made smaller than that of the moving part. By thus employing a leaf spring, not only the mass of the spring as a standalone element can be made lighter easily but also its whole length can be decreased easily, besides which the mass of the amplitude control spindle 9 can be made smaller than that of the moving part, thus realizing a linear oscillator light-weighted as a whole with an extremely small amplitude.

Figure 4:
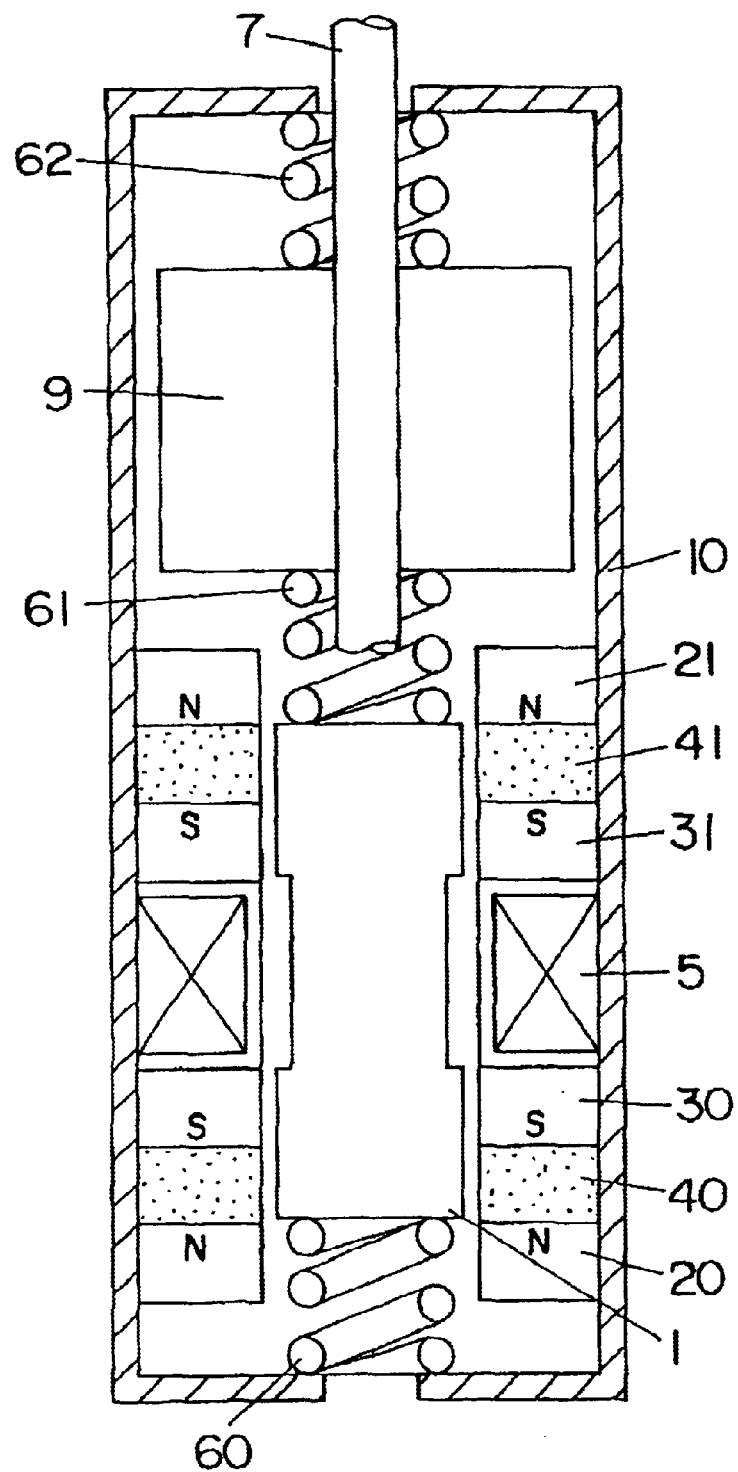
FIG. 4 is a cross-sectional view of further embodiment of the invention.

FIG. 4 is a further embodiment in which as the connection element the output-take-out shaft 7 is provided not to the plunger 1 but to the amplitude control spindle 9. In this case also, almost the same motions can be obtained as those of the above-mentioned linear oscillator and, besides, it is possible to dispose opposite to that shown in FIG. 1 the position of the magnetic circuit portion including such as the permanent magnet 5, which is usually supposed to have a large mass, thus enhancing the gravity position in height of the equipment as a whole and the freedom degree in product designing of, e.g., a distance with respect to the power supply. Also, the light-weighting of the amplitude control spindle 9 directly leads to the increasing of the linear oscillator stroke, so that these two merits can be united easily and, further, a member to be attached to the output-take-out shaft 7 can be designed as part of a mass component of the amplitude control spindle 9, to decrease the initial mass of the amplitude control spindle 9 by that much, thus obtaining a more light-weighted and less vibrated linear oscillator.

Figure 5:
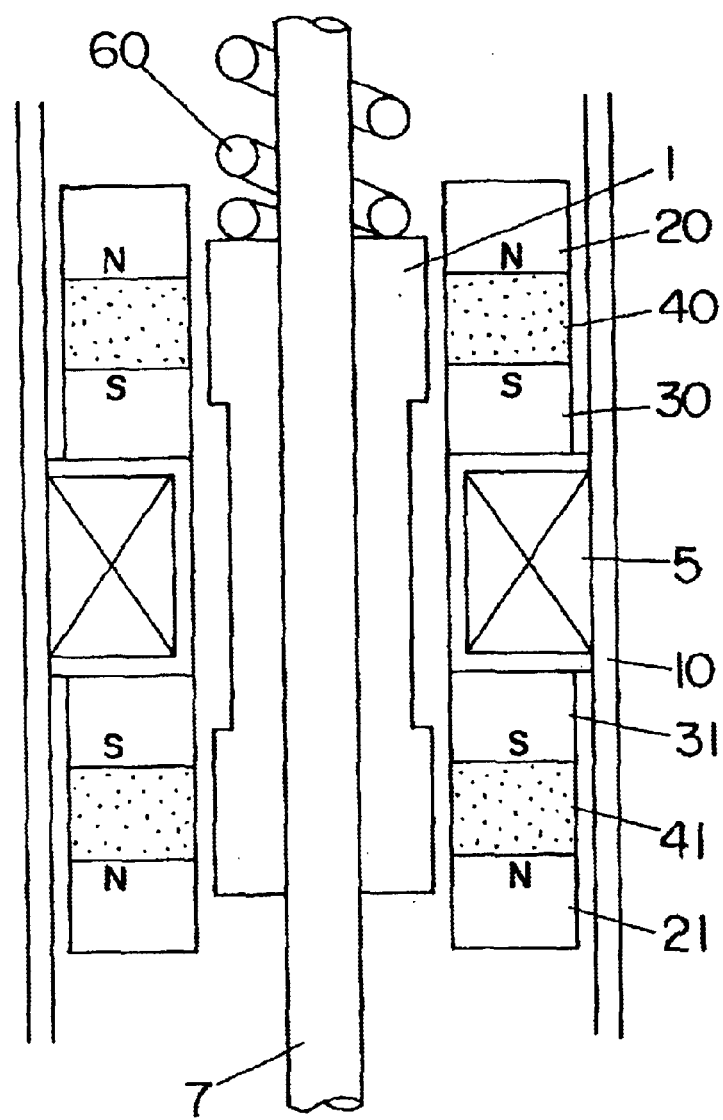
FIG. 5 is a cross-sectional view of still further embodiment of the invention.

FIG. 5 shows a still further embodiment in which the thickness of the shield case 10 formed of a magnetic substance is 7% or more of that of an outer diameter of the permanent magnets 40 and 41 and there is formed an air gap between the inner surface of the shield case 10 and the outer surface of the permanent magnets 40 and 41 and also the yokes 20, 21, 30, and 31 to thereby give a sufficient shielding effect, thus obtaining a linear oscillator having no influence on a pace maker etc. In such a case, the shielding effect is improved when at least a portion of a case such as the shield case 10 which faces the electromagnetic part is formed of a magnetic substance and has a thickness of 7% or more of the outer diameter of the permanent magnet.

Figure 6:
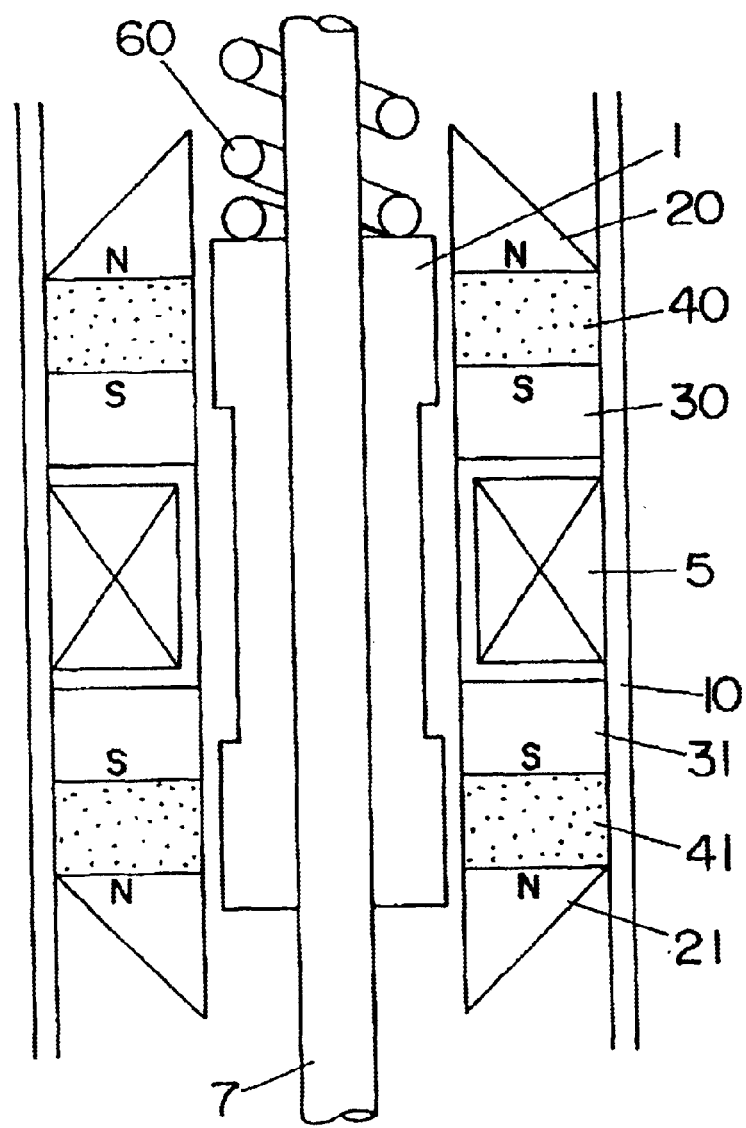
FIG. 6 is a cross-sectional view of an additional embodiment of the invention.

FIG. 6 shows an additional embodiment according to the present invention, in which the yokes 20 and 21 have a triangular cross section so that their surfaces facing the shield case 10 may be a slope. The yokes 20 and 21 and the shield case 10 can be separated from each other to thereby decrease the quantity of magnetic flux running toward the shield case 10, thus improving the driving thrust of the plunger 1, which is the moving part.

Figure 7:
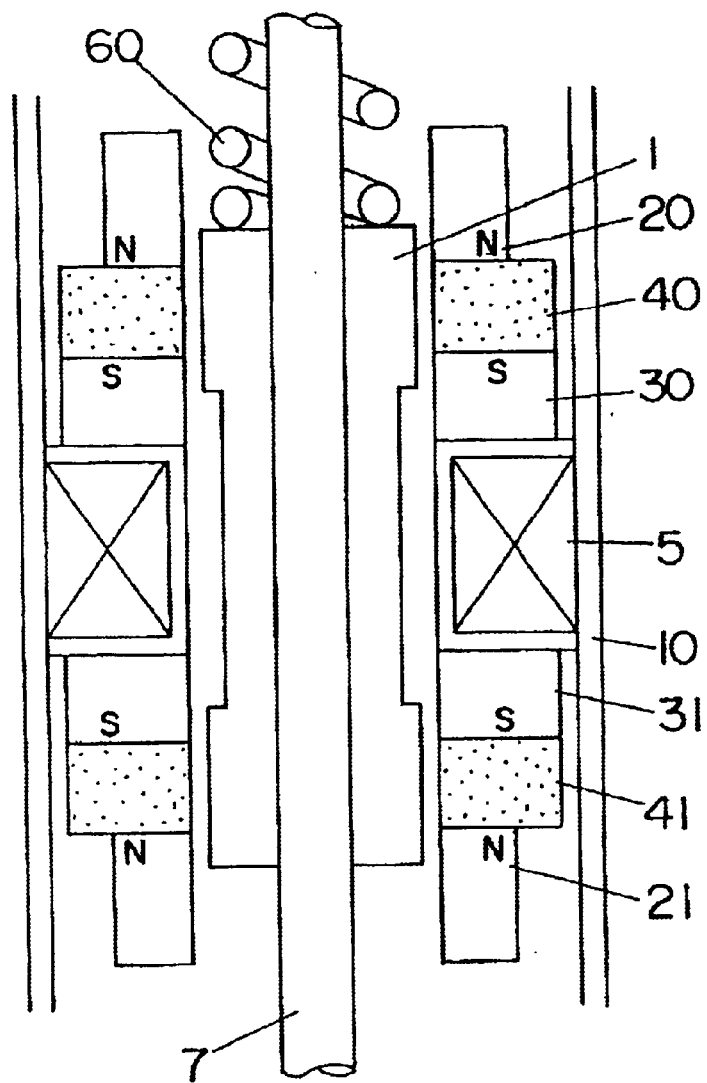
FIG. 7 is a cross-sectional view of an additional embodiment of the invention.
Figure 8:
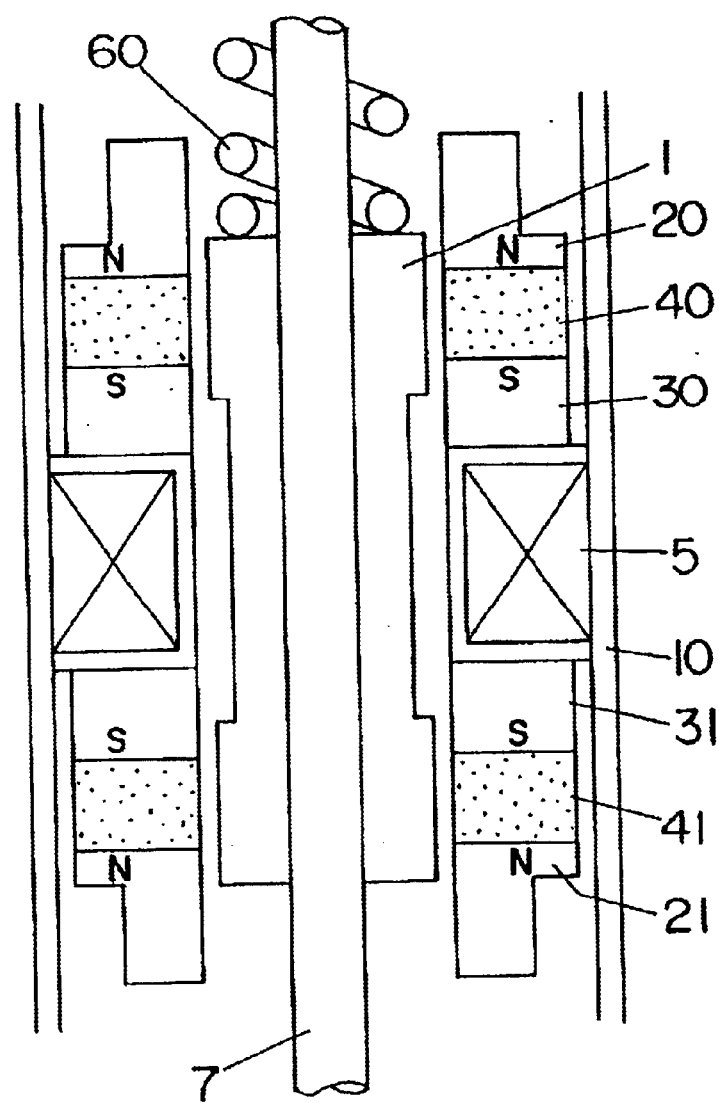
FIG. 8 is a cross-sectional view of an additional embodiment of the invention.

As shown in FIG. 7, almost the same effects as above can be obtained even when the outer diameter of the yokes 20 and 21 is made smaller than that of the permanent magnet 5 to thereby give a space with respect to the shield case 10. In this case, as shown in FIG. 8, the yokes 20 and 21 can be provided with a thin layer made of a magnetic substance covering the permanent magnet 5 entirely to thereby suppress the demagnetizing effect of the permanent magnets 40 and 41.

Figure 9:
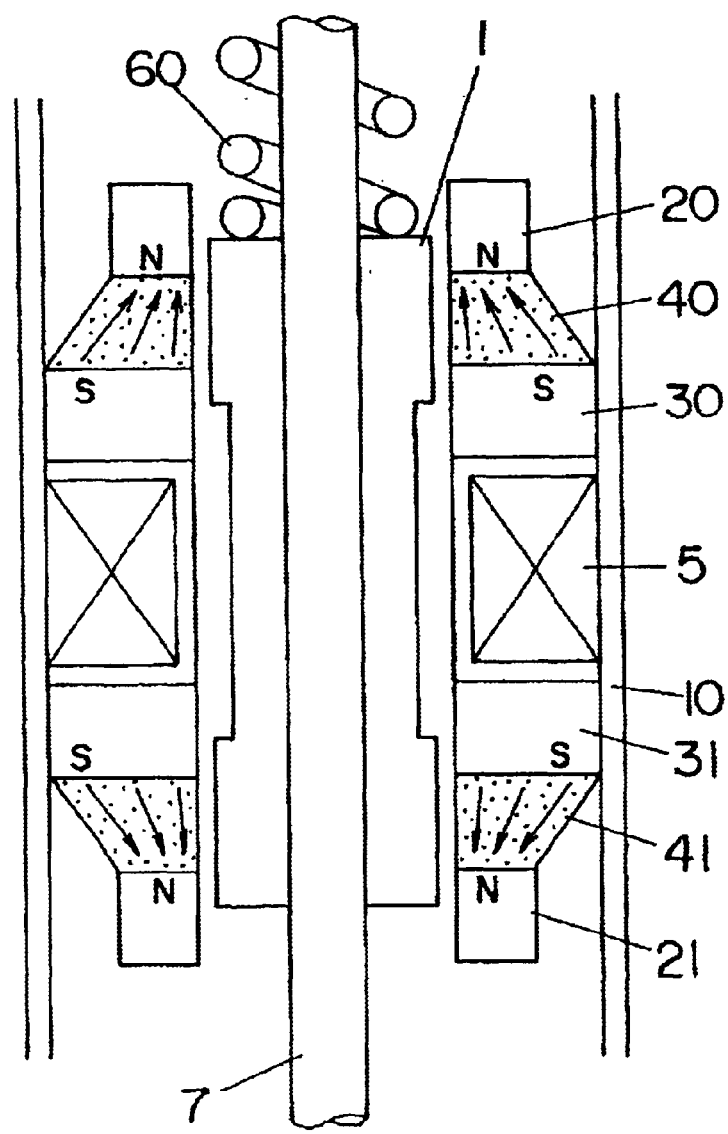
FIG. 9 is a cross-sectional view of an additional embodiment of the invention.

Besides, as shown in FIG. 9, the permanent magnets 40 and 41 can be formed frusto-conical to thereby increase the quantity of magnetic flux running toward the movable plunger 1, which contributes to the thrust.

Figure 10:
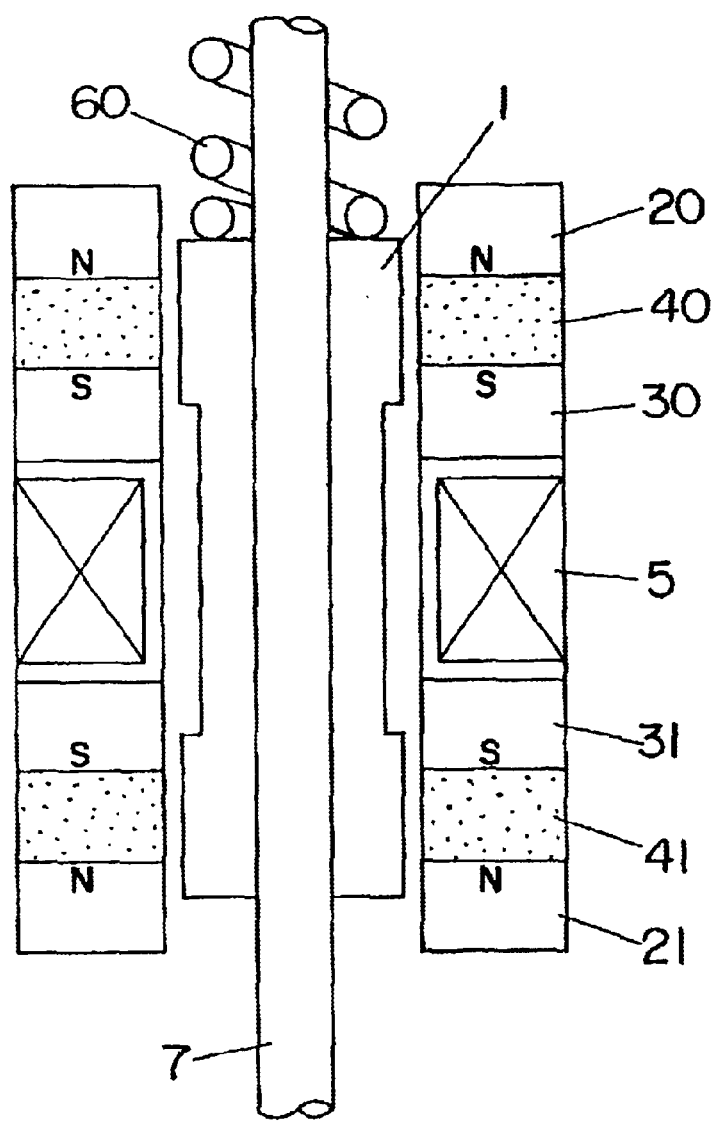
FIG. 10 is a cross-sectional view of an additional embodiment of the invention.

FIG. 10 shows an additional embodiment in which the shaft 7 passing through the movable plunger 1 is made of a nonmagnetic substance. This leads to an improvement in the thrust and also prevents the leakage of magnetic flux through the shaft 7.

Figure 11:
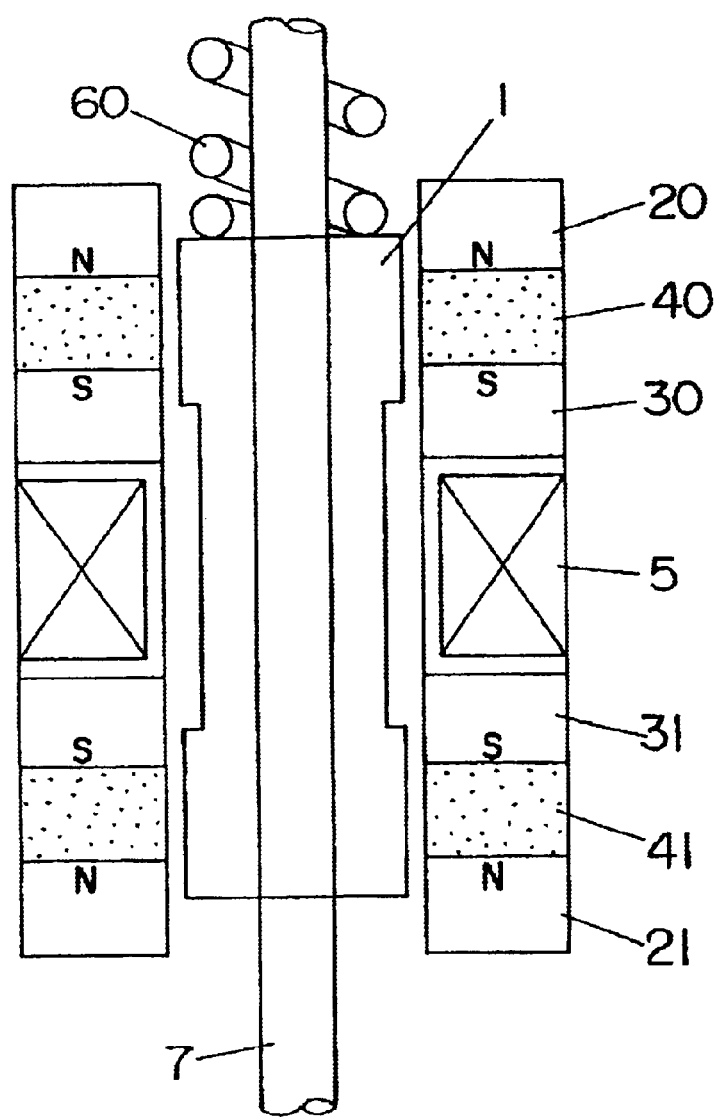
FIG. 11 is a cross-sectional view of an additional embodiment of the invention.

FIG. 11 shows an additional embodiment in which a portion of the shaft 7 which passes through the movable plunger 1 is made of a nonmagnetic substance. A portion of the plunger 1 which is exposed to the outside is made of a highly wear resistant metal material and a portion which is pressed into the plunger 1 is made of a nonmagnetic substance to thereby enable improving the thrust without deteriorating the wear resistance.

Figure 12:
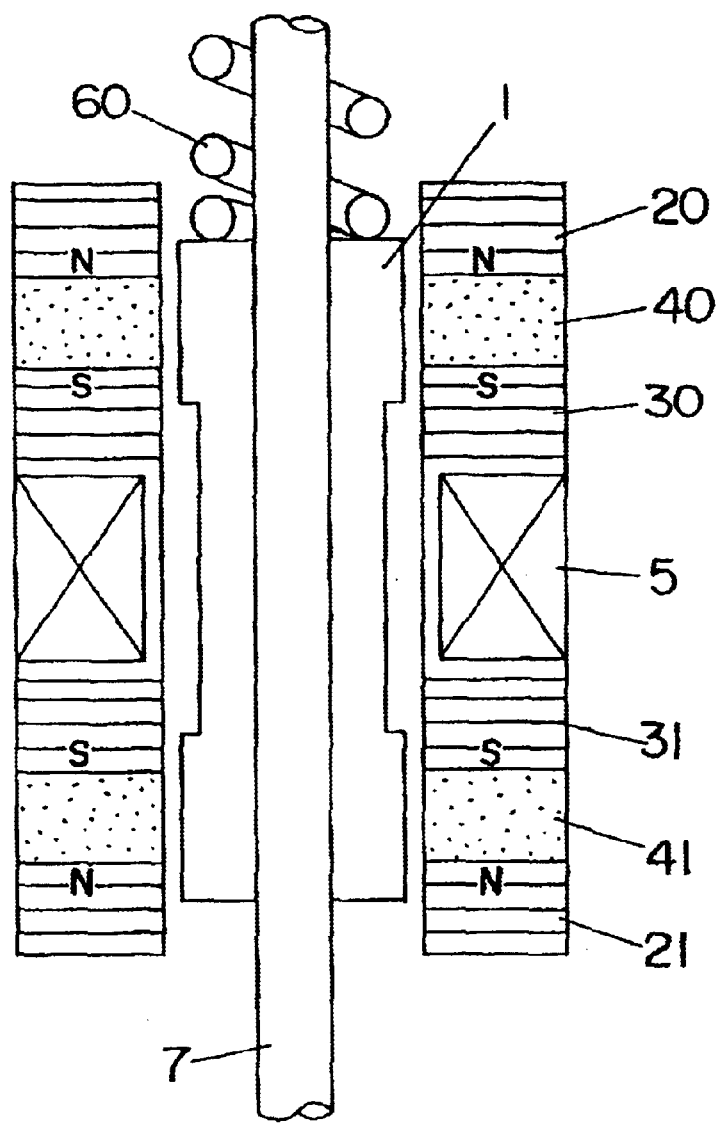
FIG. 12 is a cross-sectional view of an additional embodiment of the invention.

FIG. 12 shows an additional embodiment in which the yokes 20, 21, 30, and 31 are formed into a stack structure made of a thin sheet to thereby decrease an eddy current loss. The eddy current loss can thus be reduced and its effects increase with the increasing operating frequency. Almost the same effects can be obtained by forming the movable plunger 1 into a stacked structure. Such a structure can be formed also by blanking the material to thereby reduce the manufacturing costs.

Figure 13:
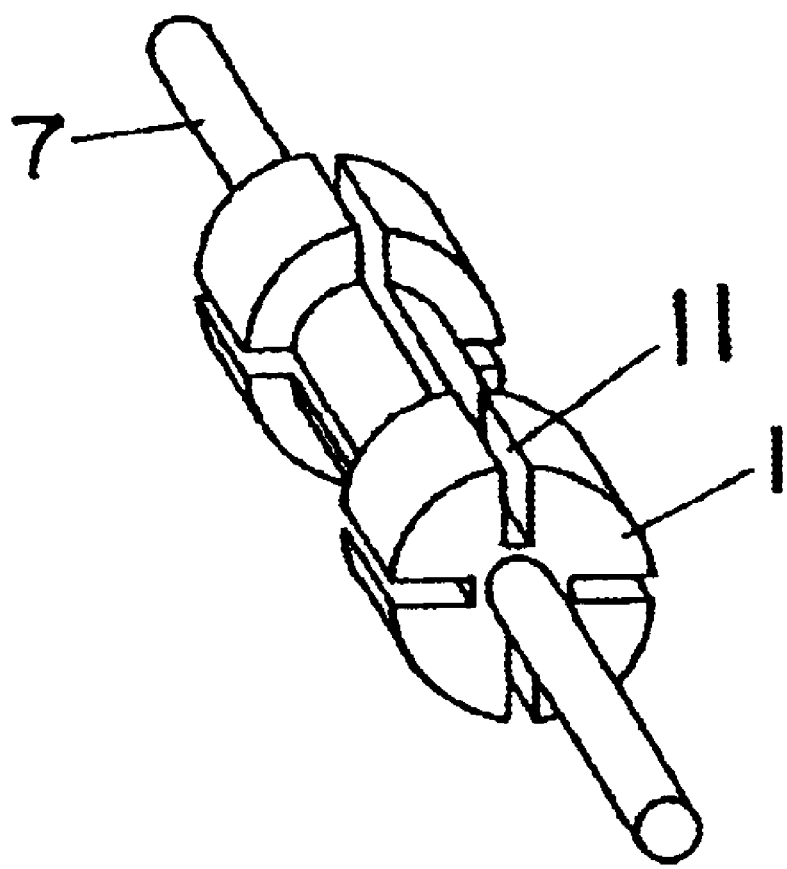
FIG. 13 is a perspective view of the plunger of the above embodiment.

FIG. 13 shows an additional embodiment in which to reduce the eddy current loss, the movable plunger 1 has a plurality of slits 11 formed therein in the amplitude direction. Those slits 11 can greatly decrease the magnitude of an eddy current when it flows in the axial direction of the plunger 1, which is the main direction in which the magnetic flux runs. In this case also, the plunger 1 can be formed into a stacked structure made of a magnetic substance to thereby mitigate the difficulty in processing and increase the demagnetizing effect due to the iron loss.

Figure 14:
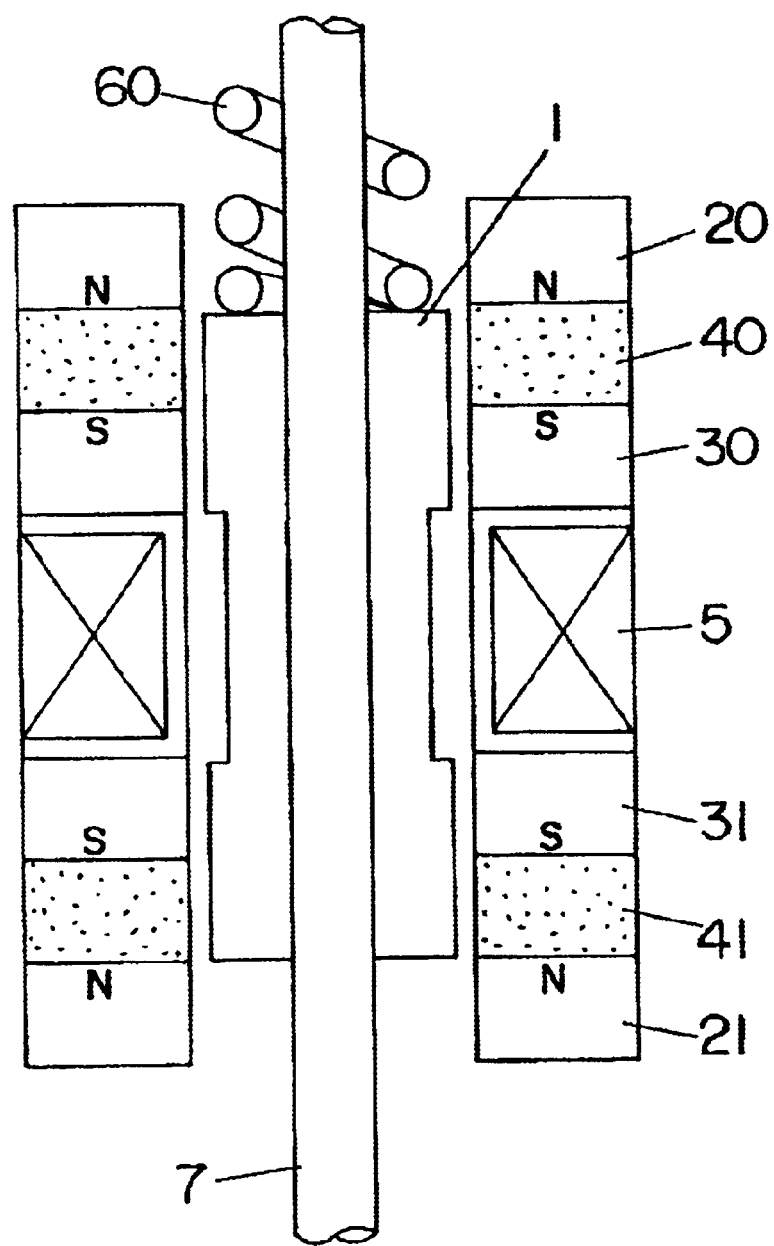
FIG. 14 is a cross-sectional view of an additional embodiment of the invention.

FIG. 14 shows an additional embodiment in which when the plunger 1 (moving part) having a large diameter portion at both ends, in its reciprocating direction, and a small diameter portion at its center is present at a neutral position, the boundary between the large diameter and small diameter portions roughly agrees with the end face of the yoke 30 and 31 on the side of the coil 5 and both axial end faces of the plunger 1 roughly agree with the end faces of the permanent magnets 40 and 41 on the sides of the yokes 20 and 21 respectively. A detent force roughly at the neutral position can be reduced to almost zero and so can be ignored in the designing of a relevant resonance system taking into account only the spring coefficient of the spring member, thus facilitating the designing.

Figure 15:
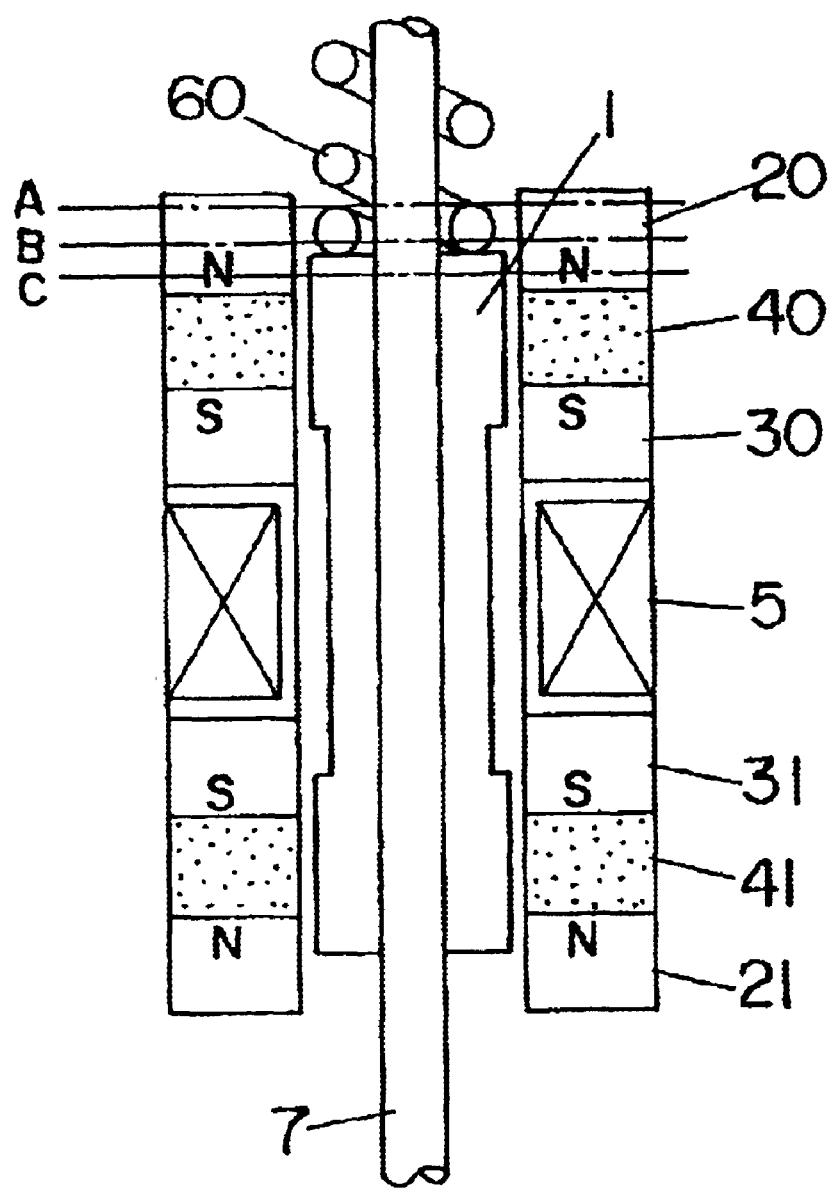
FIG. 15 is a cross-sectional view of an additional embodiment of the invention.
Figure 16:
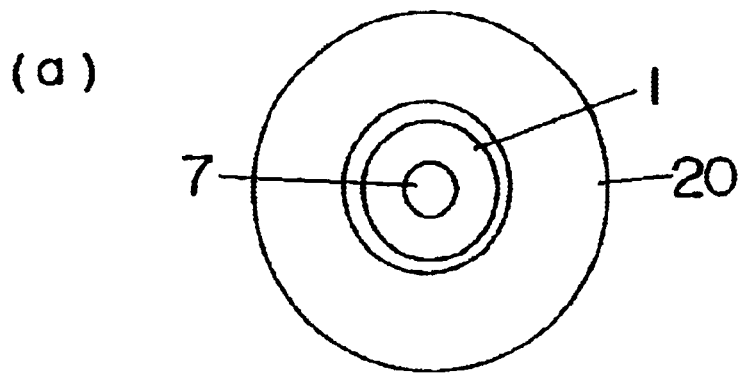
FIG. 16A is a cross-sectional view taken along line A of FIG. 15.
FIG. 16B is that taken along line B of FIG. 15.
FIG. 16C is that taken along line C of FIG. 15.
Figure 16:
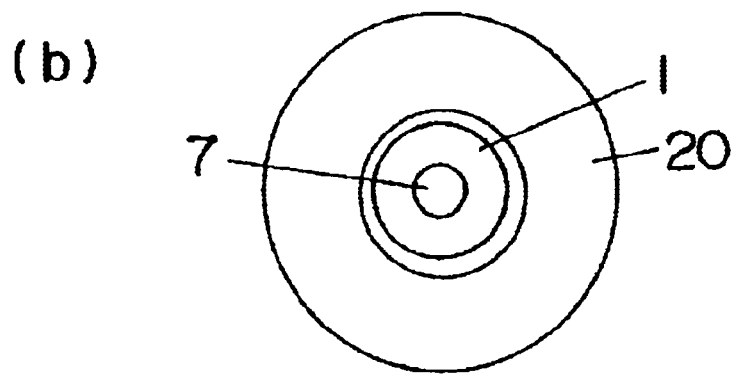
Figure 16:
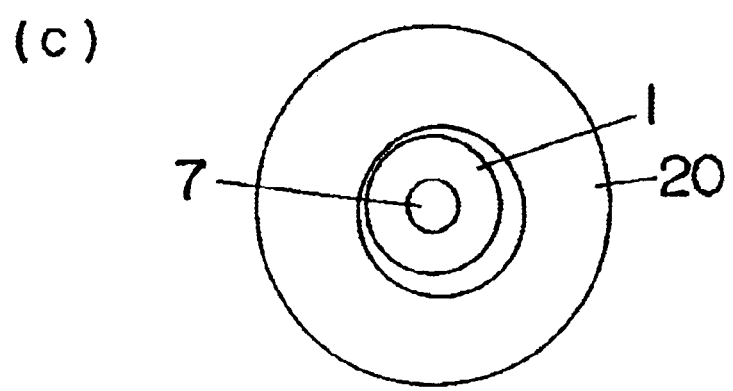

FIGS. 15 and 16 show an additional embodiment in which the air gap between the outer peripheral surface of the movable plunger 1 and the inner peripheral surface of the yokes 20 and 21 is made non-uniform in a revolution direction. FIG. 16A shows a positional relationship between the plunger and the yoke in a cross-sectional view taken along a line A of FIG. 15, FIG. 16B shows that in a cross-sectional view taken along a line B of FIG. 15, and FIG. 16C shows that in a cross-sectional view taken along a line C of FIG. 15. Since the gap between the plunger 1 and the yokes 20 and 21 changes in revolution direction with changing stroke positions, the plunger 1 can have a revolution directional force with axial movements thereof, thus obtaining a rectilinear motion as well as a revolutionary motion simultaneously.

Figure 17:
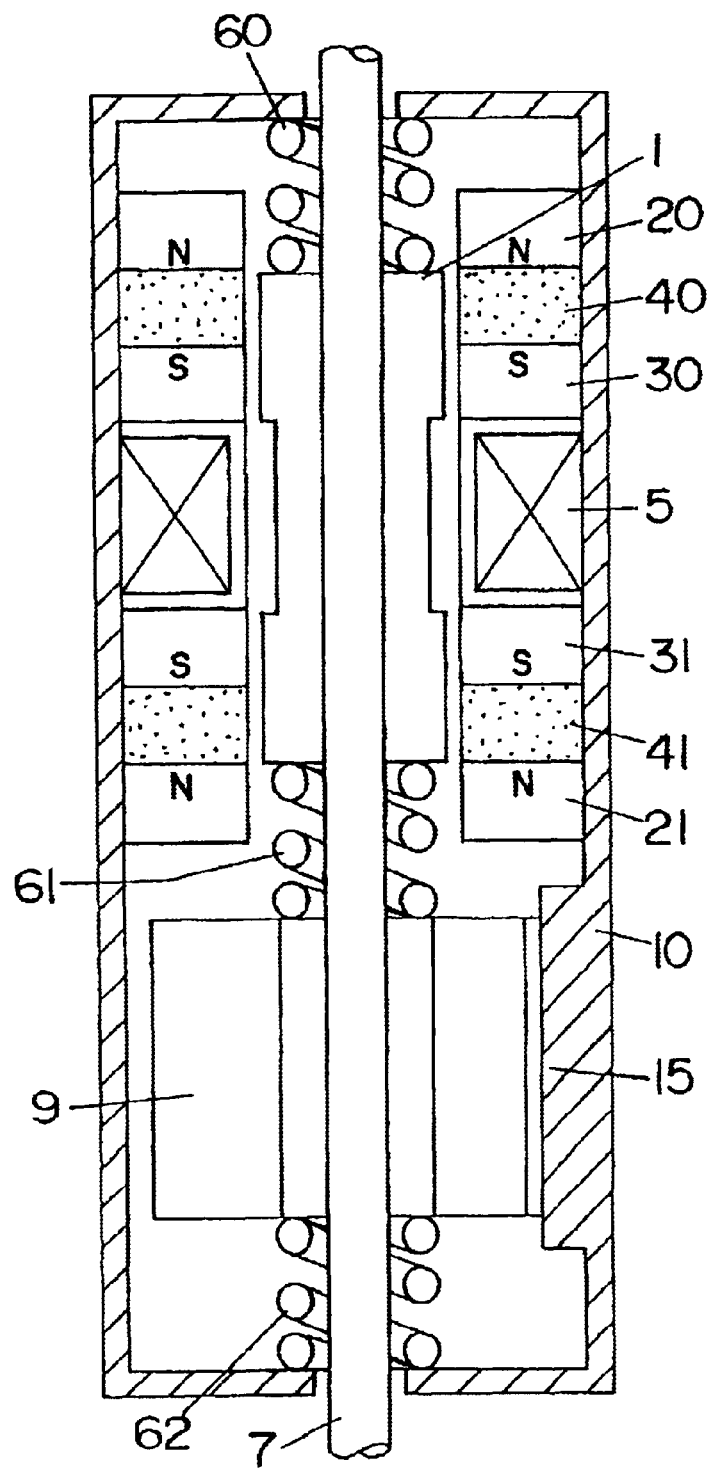
FIG. 17 is a cross-sectional view of an additional embodiment of the invention.

FIG. 17 shows an additional embodiment in which the shield case 10 has on its inner surface a guide (rocking preventing means) 15 for preventing the amplitude control spindle 9 from rocking. In this embodiment the spring member is formed of a coil spring and so the amplitude control spindle 9 may not carry out an ideal rectilinear motion because of a problem of a stress balance and may rock, in which case the amplitude control effect such as vibration absorption cannot sufficiently be obtained, which rocking of the amplitude control spindle 9 can be prevented by the guide 15 to thereby permit the amplitude control spindle 9 to move ideally.

Figure 18:
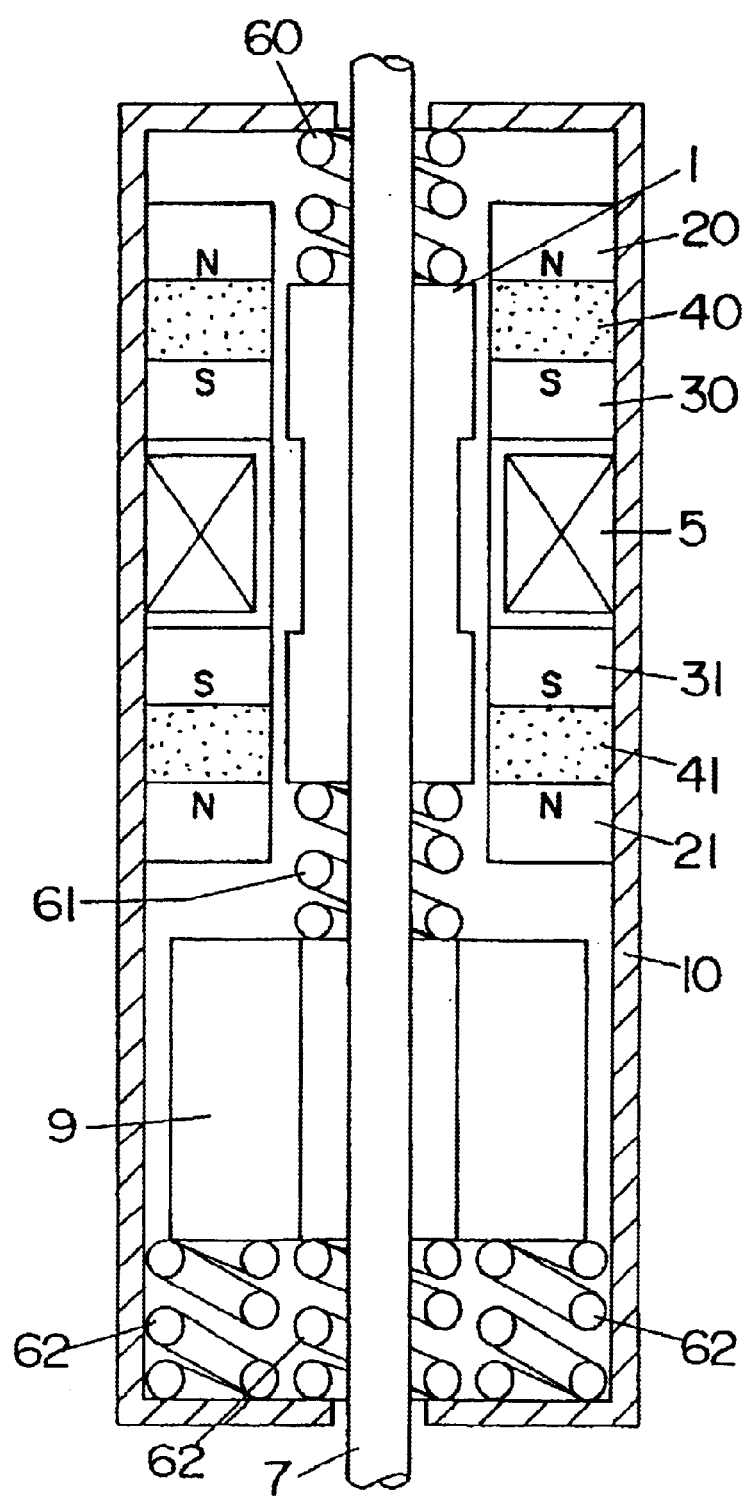
FIG. 18 is a cross-sectional view of an additional embodiment of the invention.

As shown in FIG. 18, the rocking of the amplitude control spindle 9 can be prevented also by providing the two or more spring 62 disposed between the amplitude control spindle 9 and the shield case 10.

Figure 19:
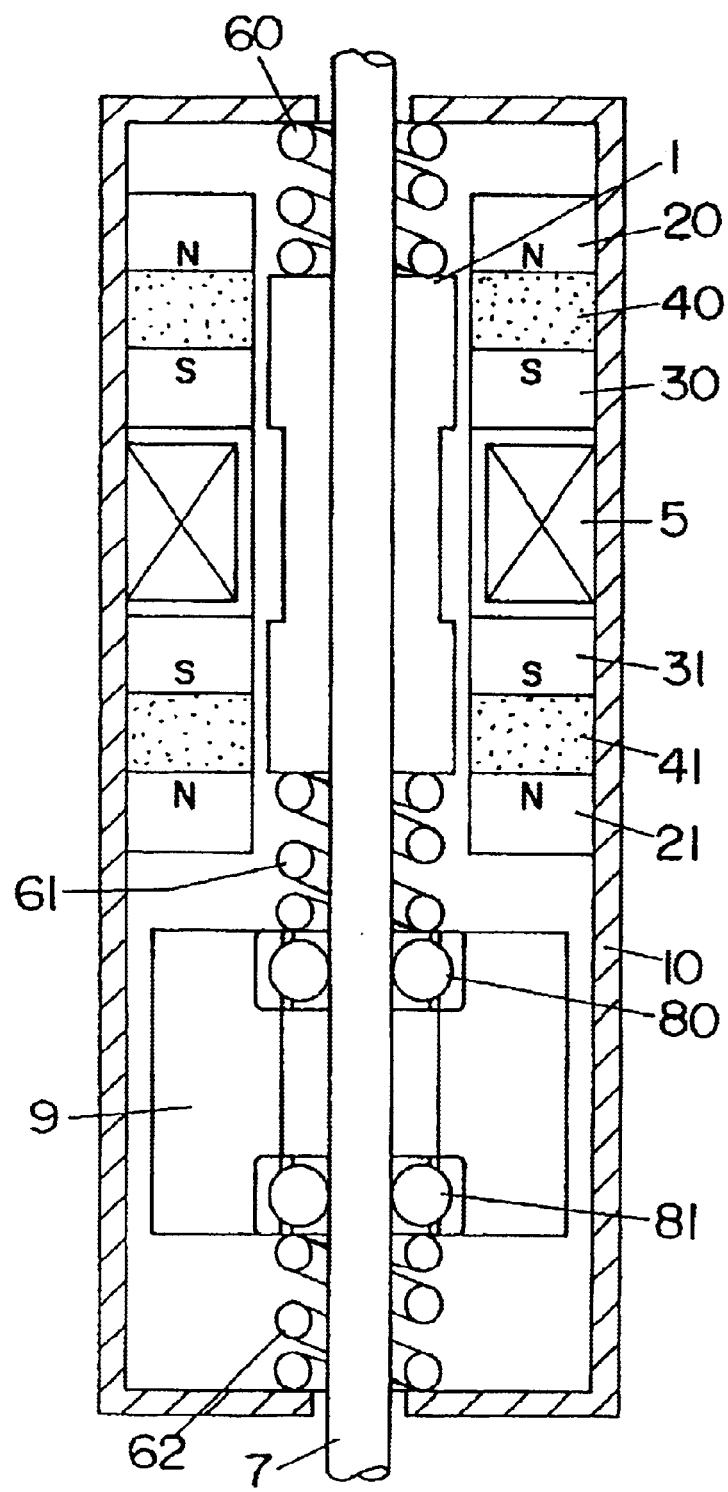
FIG. 19 is a cross-sectional view of an additional embodiment of the invention.
Figure 20:
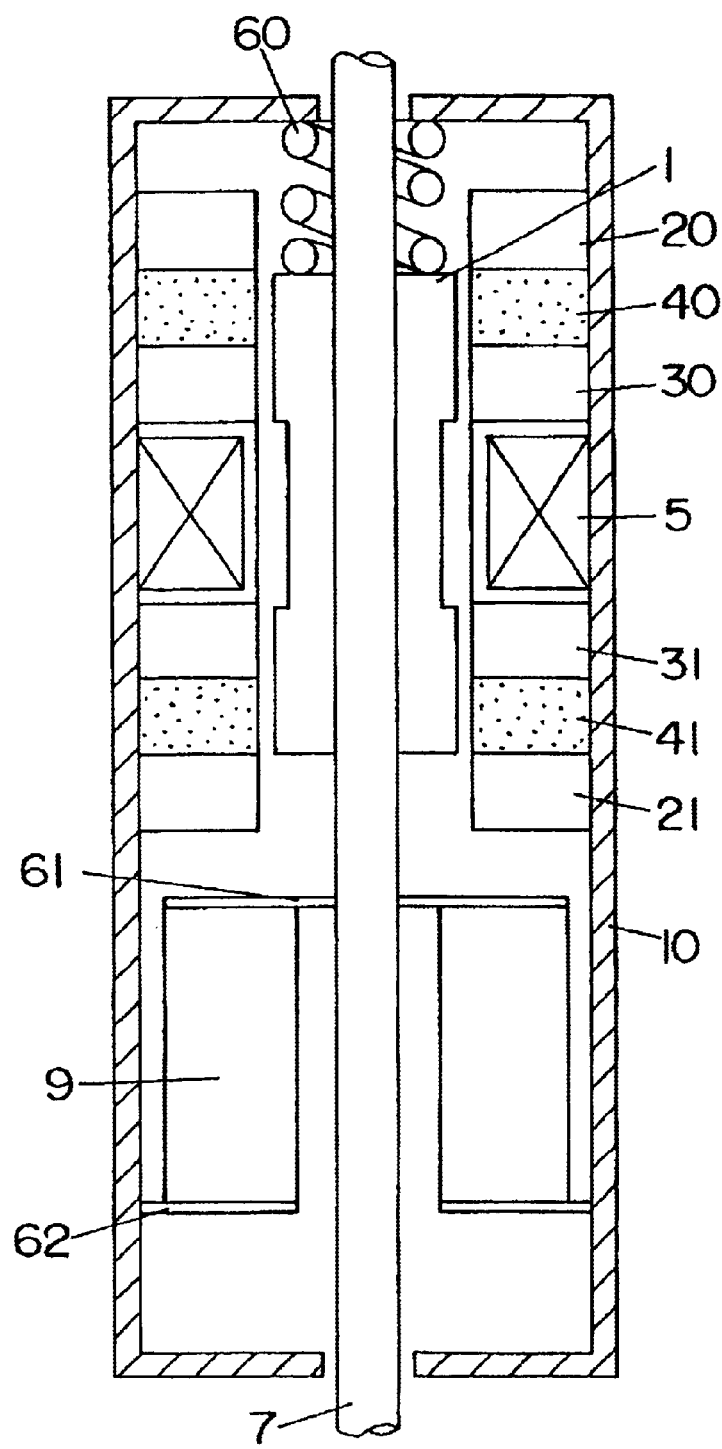
FIG. 20 is a cross-sectional view of an additional embodiment of the invention.

Also, as shown in FIG. 19, the rocking may be prevented by providing sliding bearings 80 and 81 facing the shaft 7 in the amplitude control spindle 9. A leaf spring, if used to form the spring member, would absorb the rocking, so that as shown in FIG. 20, the springs 61, 62 of the spring member which have one end thereof fixed to the amplitude control spindle 9 may be formed of the leaf spring to effectively prevent the rocking.

Figure 21:
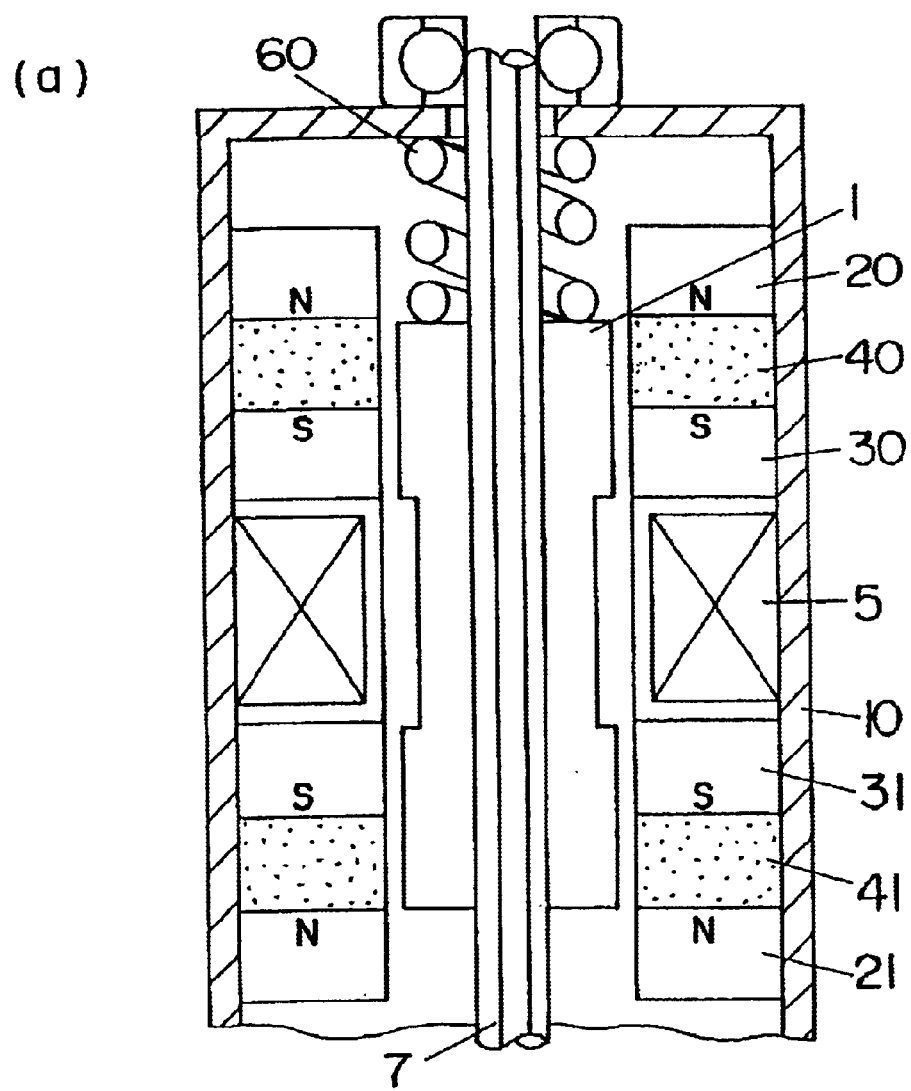
FIG. 21A is a cross-sectional view of an additional embodiment and FIG. 21B, a partial end elevation thereof.
Figure 21:
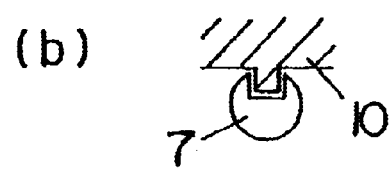

FIG. 21 shows an additional embodiment in which a groove 70 formed in the shaft 7 is engaged with a protrusion provided on the shield case 10 to thereby restrict the axial revolution of the shaft 7 and the plunger 1 around that shaft (to provide a revolution restricting means). This mechanism can suppress unnecessary axial revolutions.

Figure 22:
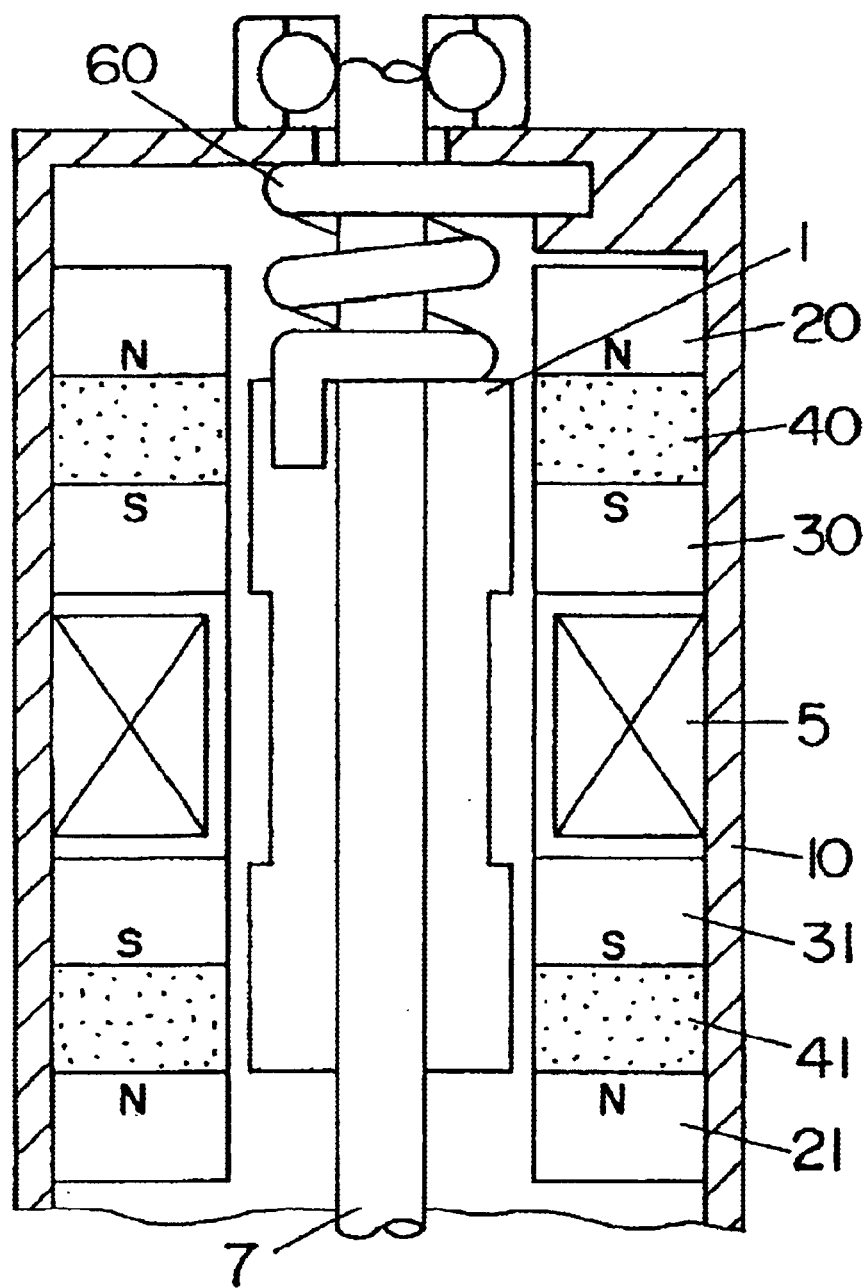
FIG. 22 is a cross-sectional view of an additional embodiment.

FIG. 22 shows an additional embodiment in which one end of the spring 60 formed of a coil spring is fixed to the shield case 10 and the other end thereof, to the plunger 1. In this case, the spring 60 formed of a coil spring not only exerts a spring force in the axial direction of the plunger 1 but also provides the plunger 1 with a small-angle reciprocating revolution in the axial direction with axial compression and expansion. In this case, the spring 60 has a spring force also in the revolution direction, thus being able to give also a secured revolutionary motion by matching a revolutionary directional resonance frequency.

As described above, according to the invention claimed here, it is possible to directly convert electric energy into a rectilinear reciprocating motion of the plunger without a motion converting mechanism for converting a revolutionary motion into a rectilinear motion and also cancel an unnecessary vibration using the amplitude control spindle in order to obtain a miniaturized linear oscillator with low noise and extremely low vibration, which is well suited for use as a driving part for mechanical control use or a driving part of an electric razor or a power tooth brush.

According to another aspect of the invention, besides the above-mentioned effects of the invention, it is possible to increase the stroke of the moving part.

According to another aspect of the invention, besides the above-mentioned effects of the invention, it is possible to suppress the rocking of the amplitude control spindle to thereby permit the amplitude control spindle to carry out in an ideal rectilinear motion, thus obtaining a sufficient vibration reducing effect.

According to another aspect of the invention, besides the above-mentioned effects of the invention, it is possible to increase a stroke of the moving part.

According to another aspect of the invention, besides the above-mentioned effects of the invention, it is possible to obtain a light-weighted and easy-to-use linear oscillator.

According to another aspect of the invention, besides the above-mentioned effects of the invention, it is possible to obtain such a linear oscillator that has an improved magnetizing effect and has a magnetic leakage level low enough to have no influence on a pace maker etc.

According to another aspect of the invention, besides the above-mentioned effects of the invention, it is possible to improve the thrust.

According to another aspect of the invention, besides the above-mentioned effects of the invention, it is possible to further improve the thrust.

According to another aspect of the invention, besides the above-mentioned effects of the invention, it is possible to improve the thrust and prevent magnetic flux leakage.

According to another aspect of the invention, besides the effects of claim 15 above, it is possible to improve the thrust without deteriorating a wear resistance.

According to another aspect of the invention, besides the above-mentioned effects of the invention, it is possible to decrease an eddy current loss.

According to another aspect of the invention, besides the effects of described above, it is possible to greatly decrease an eddy current using slits when magnetic flux runs in a direction in which the moving part moves.

According to another aspect of the invention, besides the above-mentioned effects of the invention, it is possible to reduce a detent force almost to zero at the neutral position to thereby facilitate, e.g. designing of a resonance system.

According to another aspect of the invention, besides the above-mentioned effects of the invention, it is possible to generate a revolutionary directional force according to a stroke position to thereby carry out a rectilinear motion and a revolutionary motion simultaneously.

According to another aspect of the invention, besides the above-mentioned effects of the invention, it is possible to restrict the revolution of the shaft to thereby suppress unnecessary revolution of the shaft.

According to another aspect of the invention, besides the effects of described above, it is possible to restrict revolution without any other member.

Explanation of Reference Numerals 1 plunger,
5 coil,
7 shaft,
9 amplitude control spindle, and
10 shield case.

What is claimed is:

1. A linear oscillator comprising:
   a moving part reciprocating;
   a case containing incorporating said moving part; and
   an amplitude control spindle supported in said case to be movable,
   wherein said moving part and said amplitude control spindle reciprocate at a resonance frequency of said linear oscillator or a frequency in a vicinity thereof;
   an electromagnetic driving part housed in said case, for reciprocating said moving part; and
   a spring member disposed at least between said case and said moving part, and between said case and said amplitude control spindle, for forming a spring oscillation system,
   wherein a resonance frequency of said spring oscillation system is equal to a resonance frequency of said linear oscillator or a frequency in a vicinity thereof,
   wherein said spring member includes:
      a first spring disposed between a fixed part comprised of said case and said electromagnetic driving part and said moving part;
      a second spring disposed between said moving part and said amplitude control spindle; and
      a third spring disposed between said amplitude control spindle and said fixed part.

2. The linear oscillator according to claim 1, wherein said second spring is stronger in spring force than said first and third springs.

3. A linear oscillator comprising:
   a moving part reciprocating;
   a case containing incorporating said moving part; and
   an amplitude control spindle supported in said case to be movable
   wherein said moving part and said amplitude control spindle reciprocate at a resonance frequency of said linear oscillator or a frequency in a vicinity thereof;
   an electromagnetic driving part housed in said case, for reciprocating said moving part; and
   a spring member disposed at least between said case and said moving part, and between said case and said amplitude control spindle, for forming a spring oscillation system,
   wherein a resonance frequency ef said spring oscillation system is equal to a resonance frequency of said linear oscillator or a frequency in a vicinity thereof;
   wherein:
      said spring member is formed of a leaf spring; and
      mass of said amplitude control spindle and a connection element thereof is smaller than mass of said moving part and an element thereof.

4. A linear oscillator comprising:
   a moving part reciprocating;
   a case containing incorporating said moving part; and
   an amplitude control spindle supported in said case to be movable,
   wherein said moving part and said amplitude control spindle reciprocal, at a resonance frequency of said linear oscillator or a frequency in a vicinity thereof;
   an electromagnetic driving part housed in said case, for reciprocating said moving part; and
   a spring member disposed at least between said ease and said moving part, and between said case and said amplitude control spindle, for forming a spring oscillation system,
   wherein a resonance frequency of said spring oscillation system is equal to a resonance frequency of said linear oscillator or a frequency in a vicinity thereof,
   wherein said electromagnetic driving part includes a coil to thereby use a coil current, thus enabling controlling a reciprocating motion,
   wherein said electromagnetic driving part includes:
      a coil surrounding an outer periphery of said moving part;
      second yokes each disposed at each of both ends of said coil;
      a pair of permanent magnets which are each disposed on an end face of each of said second yokes and which are magnetized symmetrically with respect to a center of said coil; and
      first yokes provided on sides of said permanent magnets opposite to said second yokes respectively.

5. The linear oscillator according to claim 4, wherein at least a portion of said case facing said electromagnetic driving part is made of a magnetic substance and a thickness of a magnetic substance facing said electromagnetic driving part is 7% or more of an outer diameter of said permanent magnets.

6. The linear oscillator according to claim 4, wherein magnetic flux increasing means is provided for increasing a quantity of magnetic flux running toward said moving part.

7. The linear oscillator according to claim 4, wherein said first yokes each have a triangular cross section having a side facing said case being a slope.

8. The linear oscillator according to claim 4, wherein said yokes or said moving part are provided with eddy current loss reducing means for reducing an eddy current loss.

9. The linear oscillator according to claim 8, wherein said moving part has a alit formed therein in an amplitude direction.

10. The linear oscillator according to claim 4, wherein said moving part has a large diameter portion at both ends thereof in a reciprocating direction thereof and a small diameter portion at a center thereof in such a configuration that a boundary between said large diameter portion and said small diameter portion may roughly agrees with an end face of said second yoke on a side of said coil and that both end faces of said moving part in a reciprocating direction roughly agree with end faces of said permanent magnets on sides of eaid first yokes.

11. The linear oscillator according to claim 4, wherein a gap between an outer peripheral surface of said moving part and an inner peripheral surface of said yokes is non-uniform in an revolutionary direction.

* * * * *